Jan. 1, 1957 F. W. ANDERSON Plant Pat. 1,543

NECTARINE TREE

Filed Nov. 18, 1955

WITNESS

Addison E. Avery

INVENTOR

Frederic W. Anderson

Webster & Webster

ATTYS.

United States Patent Office

Plant Pat. 1,543
Patented Jan. 1, 1957

1,543

NECTARINE TREE

Frederic W. Anderson, Merced, Calif.

Application November 18, 1955, Serial No. 547,877

1 Claim. (Cl. 47—62)

This invention relates to a new and distinct variety of nectarine tree which is characterized, as to primary novelty, by very early ripening, yellow fleshed, highly colored fruit.

As compared with the John Rivers nectarine (unpatented), the fruit of the present variety is yellow instead of white fleshed; ripens three or four days earlier; has more red exterior color; and has a much shorter chilling requirement during the winter months, so that its average production is greater.

As compared with the Grand River nectarine (United States Plant Patent No. 1,248), the tree of the present variety is more vigorous and productive; and the fruit, while not quite as large or as firm, is generally of better eating quality, and has less growth cracks during wet harvest seasons.

Another distinguishing characteristic of the present variety of nectarine is that the kernels or pits from the stones of the fruit are sweet, as in the case of commercial almonds.

The herein claimed variety of nectarine tree was originated by me in my experimental orchard near Le Grand, California, during the course of a continuing plant breeding program which I have conducted over a long period of years, and the purpose of which program is to seek and bring forward new and commercially desirable fruit varieties, especially peaches and nectarines, adapted for commercial planting.

In the present instance the variety was originated by me—under careful supervision and controls—by crossing the flowers of a Le Grand nectarine (United States Plant Patent No. 549) with pollen of the John Rivers nectarine. Seeds from this cross were planted, and all of the resulting seedling trees produced white fleshed nectarines. Nextly, seeds of such white fleshed nectarines were planted and the resulting seedling trees, of which about one-fourth were yellow fleshed nectarines, were brought into production in a nursery row, as well as being top-worked—by budding—on mature orchard trees in my experimental orchard, as aforesaid. One of such yellow fleshed nectarines, which is the present variety, evidenced a very early ripening period and the other described novel characteristics; all of which made the variety commercially desirable.

The asexual reproduction of the instant variety of nectarine, by budding as aforesaid, carried forward and maintained true all of the characteristics of the seedling parent.

Figure 1:
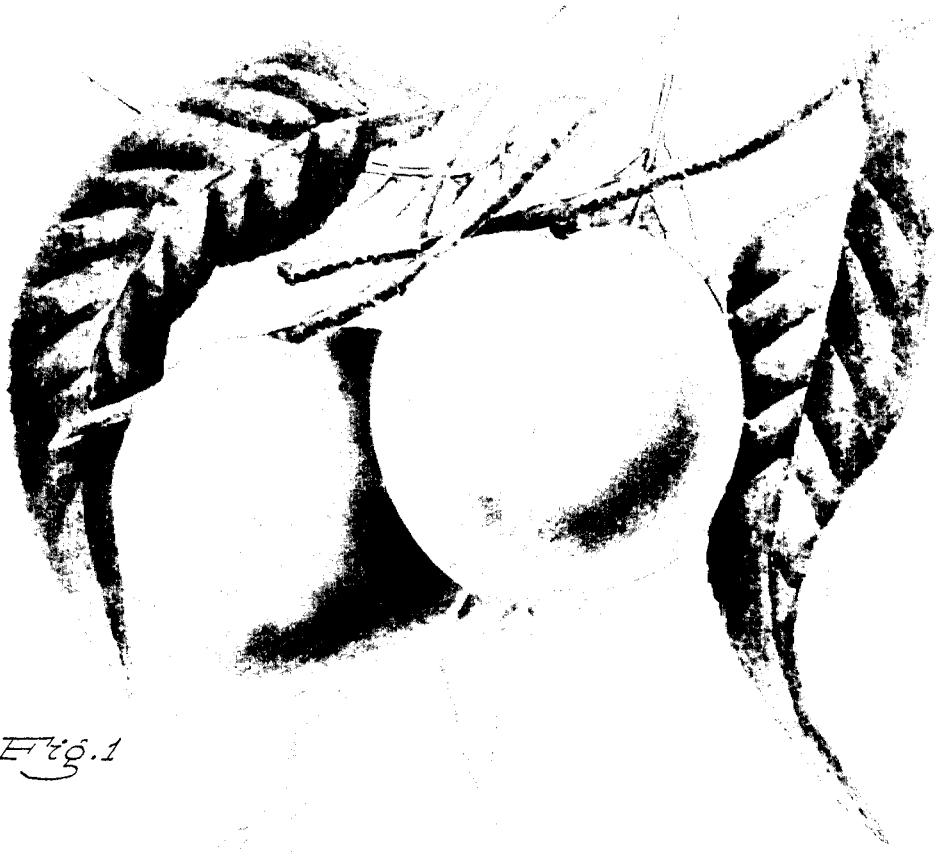
Fig. 1 is an elevation showing two of the fruit, together with twigs and leaves.
Figure 2:
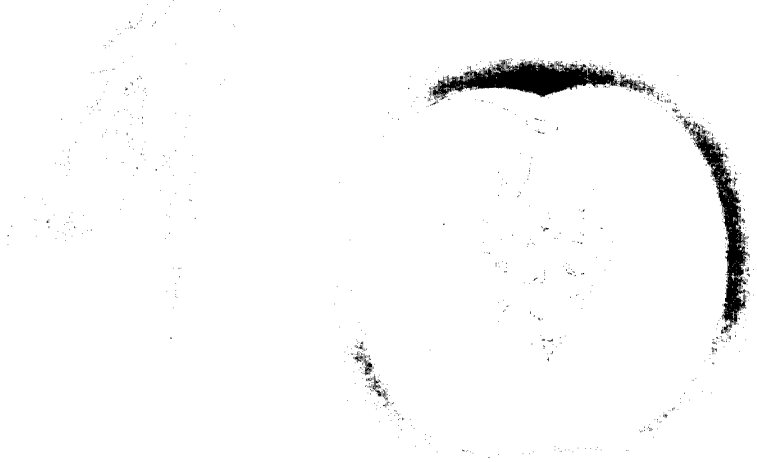
Fig. 2 is a sectional elevation of one of the fruit, with the stone exposed.

Referring now more specifically to the pomological details of this new and distinct variety of nectarine tree, the following is an outline description thereof; all major color plate identifications being by reference to Maerz and Paul Dictionary of Color:

Tree:
- *Size.*—Large to medium.
- *Vigor.*—Vigorous.
- *Growth.*—Upright to spreading.
- *Production.*—Productive.
- *Bearing.*—Regular bearer.

Trunk: *Size*—stocky to medium.

Branches: *Size*—medium.

Leaves:
- *Size.*—Medium. Average length—6½". Average width—1⅜".
- *Thickness.*—Medium.
- *Color.*—Top side—medium green (22–L–6). Under side—lighter green (21–L–6).
- *Margin.*—Crenate.
- *Petiole.*—Medium length.
- *Glands.*—Average number—four; medium size; reniform. Usually positioned two on petiole and two or three on blade.

Flower buds:
- *Size.*—Medium.
- *Length.*—Medium.
- *Form.*—Conic.

Flowers:
- *First and full bloom.*—About three or four days before the Elberta peach (unpatented). Early to medium blooming period compared with other varieties.
- *Size*—Large.

Fruit:
- *Maturity when described.*—Eating ripe.
- *Date of first picking.*—June 20, 1955.
- *Date of last picking.*—June 30, 1955.
- *Size.*—Uniform; medium to small. Average diameter axially—2¼". Average transversely in suture plane—2¼".
- *Form.*—Uniform; globose to oblong.
- *Suture.*—Distinct on ventral suture. Slight depression beyond pistil point.
- *Ventral surface.*—Rounded slightly; lips equal.
- *Cavity.*—Elongated in suture plane, with suture showing on one side. Average depth—⅜"; average breadth—⅛". Markings—usually red in color.
- *Base.*—Rounded.
- *Apex.*—Short.
- *Pistil point.*—Very small.

Skin:

*Texture.*—Medium thickness; medium toughness; tenacious to flesh.

*Tendency to crack.*—None in wet seasons.

*Down.*—Pubescence lacking, i. e. glabrous.

*Color.*—Yellow (9–K–4 shading to 10–K–6), over-spread to a major extend on the fruit with a bright red (4–L–10), shading on the light side toward orange (11–K–8), and on the dark side to deeper red (56–L–6).

Flesh:

*Juice.*—Abundant to moderate.

*Texture.*—Medium; melting.

*Ripens.*—Even.

*Flavor.*—Sub-acid.

*Eating quality.*—Good.

*Color.*—Yellow (11–K–5) near stone, shading darker (11–L–6) towards flesh. Surface of pit cavity—yellow.

Stone:

*Type.*—Free to semi-free.

*Size.*—Medium. Average length—1⅛"; average breadth—⅞"; average thickness—11/16".

*Form.*—Oval.

*Base.*—Straight.

*Hilum.*—Narrow; oblong.

*Apex.*—Acute.

*Sides.*—Equal.

*Surface.*—Pitted towards base.

*Pits.*—Elongated; annular. The pits or kernels are sweet.

*Tendency to split.*—Very slight.

*Color.*—Very light brown (10–E–4, shading to 11–G–7).

Use: Market; local.

Keeping quality: Medium.

Shipping quality: Medium.

The tree and its fruit herein described may vary in slight detail due to climatic and soil conditions under which the variety may be grown.

The following is claimed:

A new and distinct variety of nectarine tree, as illustrated and described, characterized by free to semi-free stone, early ripening, yellow fleshed fruit having yellow skin over-spread to a major extent with bright red and being entirely glabrous; such fruit—as compared with the John Rivers nectarine—being yellow fleshed instead of white fleshed, ripening three or four days earlier, having more red exterior color, and having a much shorter chilling requirement during the winter months; and—as compared with the Grand River nectarine—being not as large or as firm but of generally better eating quality, and having less growth cracks during wet harvest seasons; the tree of the instant variety being more vigorous and productive than the Grand River nectarine tree; and the kernels of the fruit being sweet, as in the case of commercial almonds.

No references cited.